United States Patent [19]
Tobin

[11] Patent Number: 5,431,859
[45] Date of Patent: Jul. 11, 1995

[54] AIR FRESHENER

[76] Inventor: Jerry Tobin, 879 River Rd., Piscataway, N.J. 08854

[21] Appl. No.: 174,328

[22] Filed: Dec. 30, 1993

[51] Int. Cl.6 ............................................... B01F 3/04
[52] U.S. Cl. .............................. 261/52; 261/DIG. 65; 422/124
[58] Field of Search .............. 261/30, 52, DIG. 65; 422/124

[56] References Cited

U.S. PATENT DOCUMENTS

| | | | |
|---|---|---|---|
| D. 321,050 | 10/1991 | Weick | 261/DIG. 65 |
| 2,460,335 | 2/1949 | Buss | 261/DIG. 65 |
| 2,678,810 | 5/1954 | Chandler | 261/DIG. 65 |
| 3,419,217 | 12/1968 | White et al. | 261/DIG. 65 |
| 3,527,405 | 9/1970 | Harding | 261/DIG. 65 |
| 4,067,692 | 1/1978 | Ferris | 261/DIG. 65 |
| 4,208,012 | 6/1980 | Dutcher | 261/DIG. 65 |
| 4,306,892 | 12/1981 | Atalkla et al. | 261/DIG. 65 |
| 4,339,079 | 7/1982 | Sato et al. | 261/DIG. 65 |
| 4,523,870 | 6/1985 | Spector | 261/DIG. 65 |
| 4,604,245 | 8/1986 | Gutierrez | 261/30 |
| 4,654,198 | 3/1987 | Berardini | 422/124 |
| 4,840,773 | 6/1989 | Wade | 422/124 |
| 4,849,606 | 7/1989 | Martens, III et al. | 219/271 |

OTHER PUBLICATIONS

American Heritage Dictionary, Apr. 1982, p. 970.

*Primary Examiner*—Tim R. Miles
*Attorney, Agent, or Firm*—Arthur L. Lessler

[57] ABSTRACT

An air freshening device employing a forced air means to diffuse air freshening material housed in the device throughout an enclosed area thereby allowing continuous freshening of the air in said enclosed area. The device is adapted to cover a heating or air conditioning vent, and may comprise either a box-like housing with adjustable front openings (FIG. 1), or a cylindrical housing (FIGS. 2 or 3) having a rotatable container therein holding an air freshening material, with cooperating adjustable slots.

1 Claim, 3 Drawing Sheets

AIR FRESHENER

FIELD OF THE INVENTION

This invention relates to an air freshening device, and more particularly to an air freshening device which utilizes a means for forcing air through said housing to freshen air.

BACKGROUND OF THE INVENTION

Air freshening devices are used to replace and mask unpleasant odors in an enclosed area such as a room with a pleasant smelling scent. Air freshening devices are also used to scent an enclosed area with a desired smell even when there is no unpleasant odor present.

One of the most commonly used air freshening devices is an aerosol in which a propellant is used to eject a disinfectant or pleasant smelling scent from a metal can or from some other type of container. Other commonly used air freshening devices include incense, powders, oils, flowers, herbs, gels or solids which are placed in a stationary spot in the area in which the air is to be freshened. Another more recent type of air freshening device involves the use of a container holding a volatile material in conjunction with an electrically heated vapor dispensing apparatus. See U.S. Pat. No. 4,849,606 entitled TAMPER-RESISTANT CONTAINER UTILIZING A FLEXIBLE SEAL issued on Mar. 20, 1979 to Edward J. Martens et al. and assigned to S. C. Johnson & Son, Inc.

All of the aforementioned air freshening devices suffer from a common drawback. They all rely on the natural air currents contained in the enclosed area in which the air freshening device is placed to diffuse the air freshening material. It is, therefore, an object of this invention to provide an air freshening device which utilizes a means for forcing air such as a central heating-/air conditioning system or car air conditioner to help diffuse the air freshening material throughout the enclosed area in which the air is to be freshened.

SUMMARY OF THE INVENTION

An air freshening device employing a forced air means to diffuse air freshening material housed in the device throughout an enclosed area in which air is to be freshened with a pleasant smelling scent.

DETAILED DESCRIPTION OF THE DRAWINGS

Figure 1:
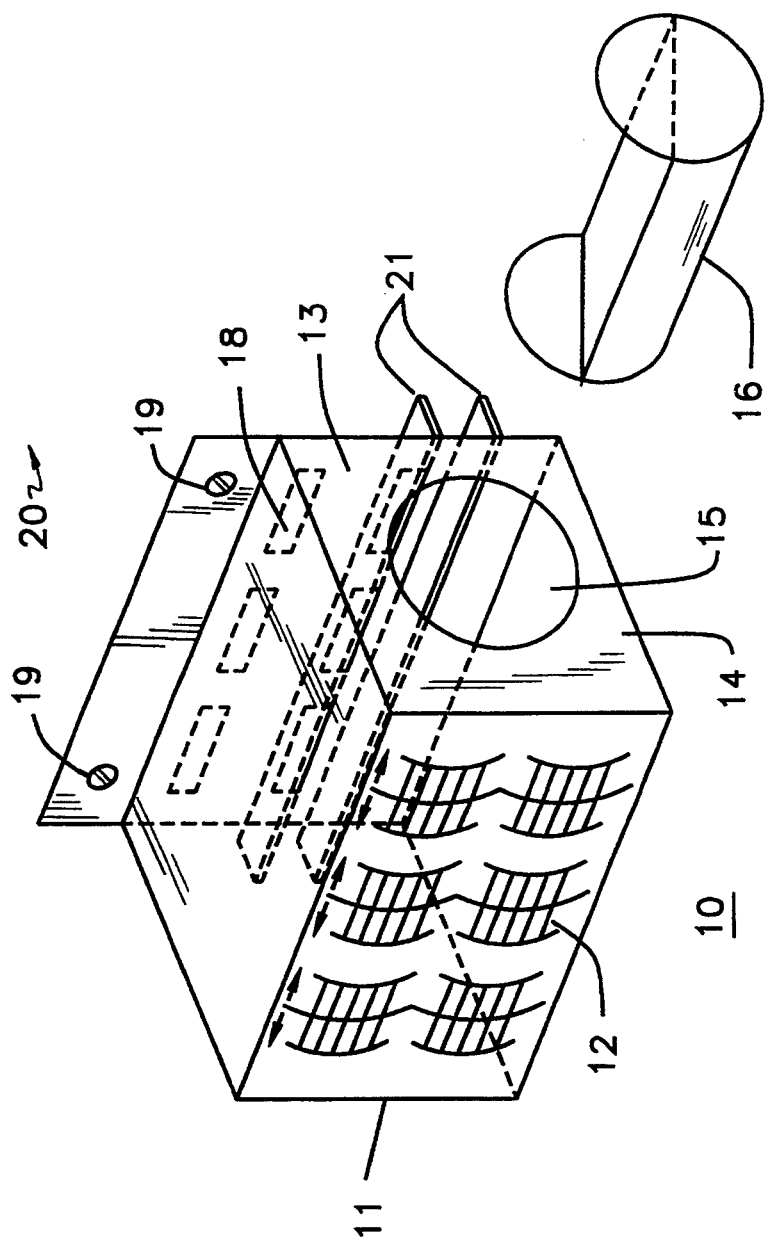
FIG. 1 shows a first embodiment of the air freshening device according to this invention.

Referring to FIG. 1 there is shown an air freshening device 10 according to the present invention. The air freshening device 10 includes a housing 11 having a front surface 12, a rear surface 13, and a side surface 14. Side surface 14 has an opening 15 into which a container 16 for holding an air freshening material can be inserted. Front surface 12 has openings 17 for air to exit from housing 11, and rear surface 13 has openings 18 for air to enter into housing 11. Openings 17 and 18 can be slits, holes or any other type of opening through which air can flow. Housing 11 can be manufactured so that a lever positioned on front surface 12 can be used to adjust openings 17 both vertically and horizontally, as well as to completely close openings 17.

To use air freshening device 10, air freshening material is placed in container 16 and container 16 is then inserted into housing 11 via opening 15 of side surface 14. The air freshening material used can be either a solid, liquid or vapor. Housing 11 is then fixedly mounted by means of screws 19 or any other mounting means to a wall 20 in the enclosed area to be freshened so that rear surface 13 covers the baffles 21 of a heating-/air conditioning vent on wall 20. Air from the heating-/air conditioning system passes through baffles 21 and into housing 11 through openings 18 of rear surface 13. The air then flows across the air freshening material in container 16 thereby becoming scented and then exits housing 11 through openings 17 of front surface 12. In so doing, pleasant smelling air can continually be provided to an enclosed area. Air freshening device 10 can be used in a home, office, car, train or any other enclosed area.

Figure 2:
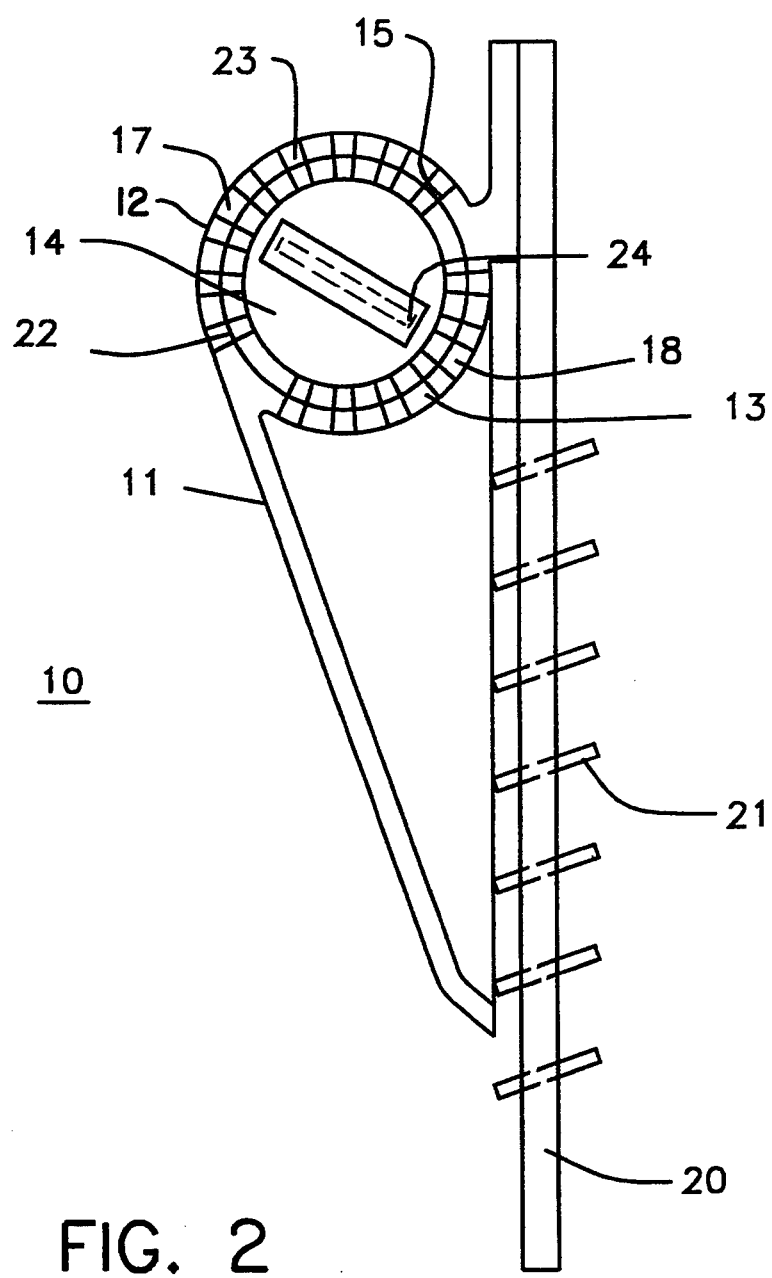
FIG. 2 shows a second embodiment of the air freshening device according to this invention in the open position.
Figure 3:
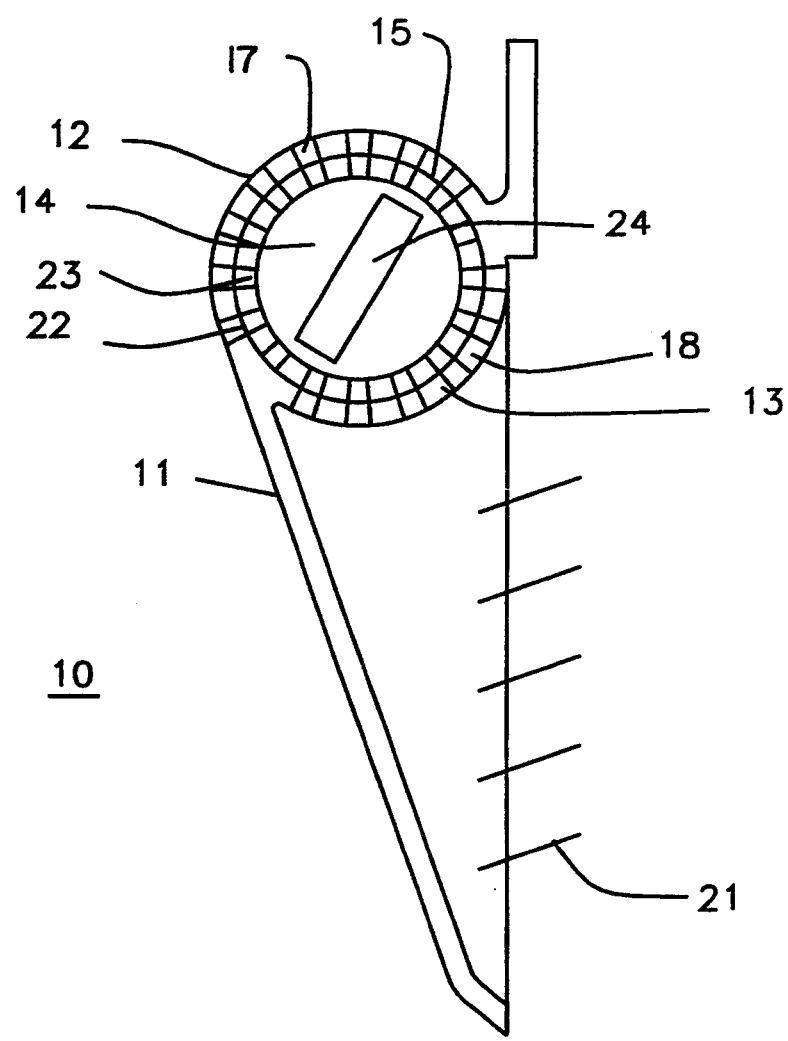
FIG. 3 shows a second embodiment of the air freshening device according to this invention in the closed position.

FIG. 2 shows an alternative embodiment of air freshening device 10 in which an enclosed container 22 is used for holding an air freshening material. Container 22 has openings 23 through which air can pass. Container 22 has one end 24 which protrudes from housing 11 when container 22 is inserted therein. By grasping end 24, container 22 can be inserted or withdrawn from housing 11 to load and unload air freshening material. End 24 can also be used to rotate container 22 within housing 11.

As shown in FIG. 2, when container 22 is rotated within housing 11 such that openings 23 are aligned with openings 17 and 18, air entering housing 11 through openings 18 can flow through container 22 and thus become scented by the air freshening material in container 22 before then exiting housing 11 via openings 17. Conversely, and as shown in FIG, 3, by rotating container 22 within housing 11 so that openings 23 are not aligned with openings 17 and 18, air can not flow through housing 1 1 and thus air freshening device 10 will not be able to freshen air. Air freshening device 10 can be placed either in front of or behind heating/air conditioning ventilation baffles, so that if one desires, air freshening device 10 can be hidden from view.

It will be understood that the embodiments described herein are merely exemplary and that a person skilled in the art may make many variations and modifications to the described embodiments utilizing functionally equivalent elements to those described. Any variations or modifications to the invention just described, including those made to the shape and/or orientation of the housing, container or openings, are intended to be included within the scope of said invention as defined by the appended claims.

I claim:

1. An air freshening device, comprising:
   a housing having a hollow cylinder portion and first and second flange members depending therefrom, said cylinder portion of said housing comprising a rear cylindrical wall having a plurality of air inlet longitudinal slots therein through which air may be introduced and a front cylindrical wall having a plurality of air outlet longitudinal slots therein through which air may be discharged, said first flange member having one end contiguous with said cylinder portion at a first longitudinally extending region between said front and rear walls, and a remote end adapted to engage a first portion of a supporting surface through which forced air may be directed toward said flange member and rear wall, said second flange member having one end contiguous with said cylinder portion at a second longitudinally extending region between said front and rear walls in opposed relationship to said first longitudinally extending region, and a remote end adapted to engage a second portion of said supporting surface, so that when said remote ends of said flanges are affixed to said supporting surface, forced air may enter the portion of said housing bounded by said first flange, said rear cylindrical wall, said second flange, and said supporting surface;

a removable cylinder-shaped container for holding air scenting material, said container having an outer diameter less than the inner diameter of said cylinder portion of said housing and being closely surrounded by said cylinder portion and coaxial therewith, said container having a plurality of longitudinal slots therein, said slots communicating with each other, said container having turning and holding means for grasping the container and manually rotating the container about the longitudinal axis thereof, the slots of said container being dimensioned and spaced apart so that as said container is manually rotated about said axis, those slots of said container which are adjacent to slots of one of said walls interact with said adjacent slots to alternately block or permit the flow of air from the portion of said housing bounded by said first flange, said rear cylindrical wall, said second flange, and said supporting surface through said container and out from the slots of said front wall;

whereby unscented air introduced into the cylinder portion of said housing through the slots in said rear wall acquires the scent of said air scenting material and then exits through the slots in said front wall.

* * * * *